US00PP35915P2

(12) United States Plant Patent
Wood

(10) Patent No.: US PP35,915 P2
(45) Date of Patent: Jul. 2, 2024

(54) ***WEIGELA* PLANT NAMED 'SMNW9RB'**

(50) Latin Name: *Weigela florida*
Varietal Denomination: SMNW9RB

(71) Applicant: Timothy D. Wood, Spring Lake, MI (US)

(72) Inventor: Timothy D. Wood, Spring Lake, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/239,954

(22) Filed: Aug. 30, 2023

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
See application file for complete search history.

(56) References Cited

U.S. PATENT DOCUMENTS

PP33,977 P2 * 3/2022 Verhoef ..... Plt./226

* cited by examiner

*Primary Examiner* — Karen M Redden
(74) *Attorney, Agent, or Firm* — C. Anne Whealy

(57) ABSTRACT

A new and distinct cultivar of *Weigela* plant named 'SMNW9RB', characterized by its upright to outwardly spreading and uniformly mounding plant habit; vigorous growth habit and rapid growth rate; freely branching habit; dense and bushy appearance; leaves that are dark green in color tinged with dark greyish brown; freely and remontant flowering habit; bright purplish red-colored flowers; and good garden performance.

2 Drawing Sheets

Figure 1:
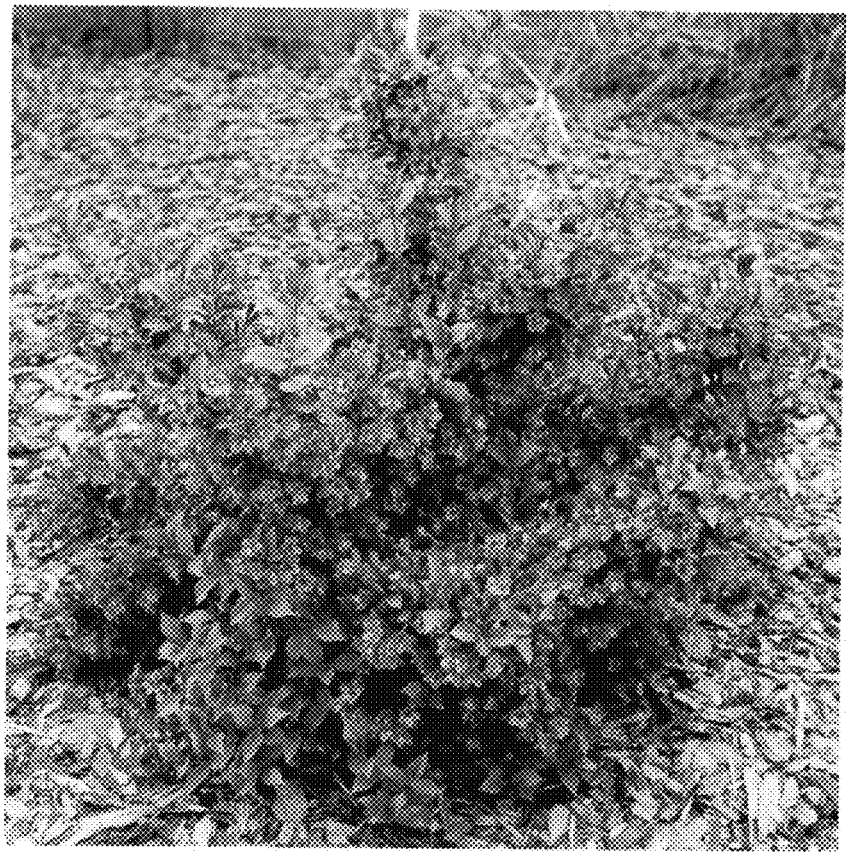

Botanical designation: *Weigela florida.*
Cultivar denomination: 'SMNW9RB'.

BACKGROUND OF THE INVENTION

The present invention relates to a new and distinct cultivar of *Weigela* plant, botanically known as *Weigela florida* and hereinafter referred to by the name 'SMNW9RB'.

The new *Weigela* plant is a product of a planned breeding program conducted by the Inventor in Grand Haven, Michigan. The objective of the breeding program was to develop new freely-flowering *Weigela* plants with dark-colored leaves and vibrant and attractive flower color.

The new *Weigela* plant originated from an open-pollination in 2014 in Grand Haven, Michigan of an unnamed proprietary selection of *Weigela florida*, not patented, as the female, or seed, parent with an unknown proprietary selection of *Weigela florida* as the male, or pollen, parent. The new *Weigela* plant was discovered and selected by the Inventor in 2016 as a single flowering plant within the progeny of the stated open-pollination in a controlled environment in Grand Haven, Michigan.

Asexual reproduction of the new *Weigela* plant by softwood stem cuttings since 2016 in Grand Haven, Michigan has shown that the unique features of this new *Weigela* plant are stable and reproduced true to type in successive generations of asexual reproduction.

SUMMARY OF THE INVENTION

Plants of the new *Weigela* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNW9RB'. These characteristics in combination distinguish 'SMNW9RB' as a new and distinct *Weigela* plant:

1. Upright to outwardly spreading and uniformly mounding plant habit.
2. Vigorous growth habit and rapid growth rate.
3. Freely branching habit; dense and bushy appearance.
4. Leaves that are dark green in color tinged with dark greyish brown.
5. Freely and remontant flowering habit.
6. Bright purplish red-colored flowers.
7. Good garden performance.

In side-by-side comparisons, plants of the new *Weigela* differ primarily from plants of the female parent selection in plant habit as plants of the new *Weigela* are more freely flowering than plants of the female parent selection.

Plants of the new *Weigela* can be compared to plants of the *Weigela hybrida* 'Bokrasopin', disclosed in U.S. Plant Pat. No. 24,572. In side-by-side comparisons plants of the new *Weigela* differ primarily from plants of 'Bokrasopin' in the following characteristics:

1. Plant habit of the new *Weigela* is less open than and not as open as plant habit of plants of 'Bokrasopin'.
2. Leaves of plants of the new *Weigela* are dark green in color tinged with dark greyish brown whereas leaves of plant of 'Bokrasopin' are dark green in color without any brownish tinging.

3. Flowers of plants of the new *Weigela* are bright reddish purple in color whereas flowers of plant of 'Bokrasopin' are red purple in color.

Plants of the new *Weigela* can also be compared to plants of the *Weigela florida* 'SMNWFG', disclosed in U.S. Plant Pat. No. 35,120. In side-by-side comparisons plants of the new *Weigela* differ primarily from plants of 'SMNWFG' in the following characteristics:

1. Leaves of plants of the new *Weigela* are not as dark in color as leaves of plant of 'SMNWFG'.
2. Flowers of plants of the new *Weigela* are darker in color than flowers of plant of 'SMNWFG'.

BRIEF DESCRIPTION OF THE PHOTOGRAPHS

The accompanying colored photographs illustrate the overall appearance of the new *Weigela* plant showing the colors as true as it is reasonably possible to obtain in colored reproductions of this type. Colors in the photographs may differ slightly from the color values cited in the detailed botanical description which accurately describe the colors of the new *Weigela* plant.

The photograph on the first sheet (FIG. 1) is a side perspective view of a typical flowering plant of 'SMNW9RB' grown in an outdoor nursery.

Figure 2:
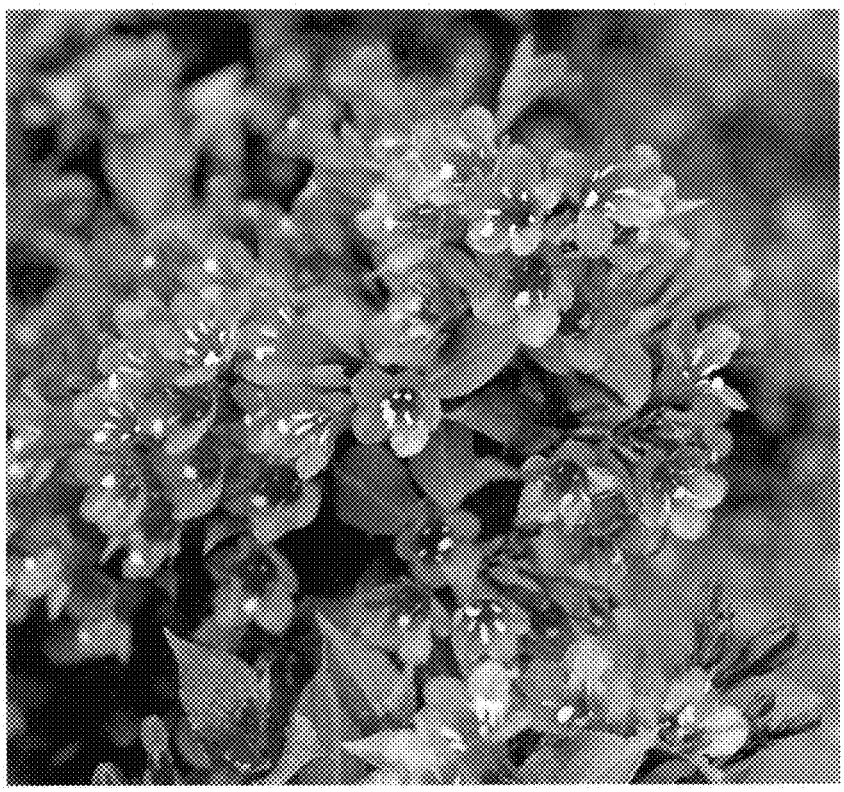

The photograph on the second sheet (FIG. 2) is a close-up view of typical flowers of 'SMNW9RB'.

DETAILED BOTANICAL DESCRIPTION

Plants used for the aforementioned photographs and the following description were grown during the spring in ground beds in an outdoor nursery in Grand Haven, Michigan and under cultural practices typical of commercial *Weigela* production. During the production of the plants, day temperatures ranged from 18 C to 27 C and night temperatures ranged from 5 C to 10 C. Plants of the new *Weigela* were four years old when the photographs and description were taken. In the following description, color references are made to The Royal Horticultural Society Colour Chart, 2015 Edition, except where general terms of ordinary dictionary significance are used.

Botanical classification: *Weigela florida* 'SMNW9RB'.

Parentage:

*Female, or seed, parent*.—Unnamed proprietary selection of *Weigela florida*, not patented.

*Male, or pollen, parent*.—Unknown proprietary selection of *Weigela florida*, not patented.

Propagation:

*Type*.—By softwood stem cuttings.

*Time to initiate roots, summer*.—About 15 days at temperatures about 18 C to 27 C.

*Time to produce a rooted young plant, summer*.—About two months at temperatures about 18 C to 27 C.

*Root description*.—Fine; fibrous; typically white in color, actual color of the roots is dependent on substrate composition, water quality, fertilizer, substrate temperature and physiological age of roots.

*Rooting habit*.—Freely branching; dense.

Plant description:

*Plant and growth habit*.—Perennial shrub; upright to outwardly spreading and uniformly mounding plant habit; vigorous growth habit and rapid growth rate.

*Branching habit*.—Freely branching habit with about 30 lateral branches developing per plant; pinching enhances lateral branch development; dense and bushy plant form.

*Plant height*.—About 63 cm.

*Plant diameter*.—About 80 cm.

Lateral branch description:

*Length*.—About 61 cm.

*Diameter*.—About 5 mm.

*Internode length*.—About 3.5 cm.

*Texture*.—Slightly pubescent on developing stems; developed stems, mostly smooth and glabrous and becoming woody with subsequent development.

*Strength*.—Strong.

*Aspect*.—About 45 to 75 degrees from vertical.

*Color*.—Close to N144D; when woody, close to N199C to N199D.

Leaf description:

*Arrangement*.—Opposite; simple.

*Length*.—About 7.25 cm.

*Width*.—About 3.4 cm.

*Shape*.—Elliptic.

*Apex*.—Acuminate.

*Base*.—Cuneate.

*Margin*.—Serrulate.

*Texture, upper surface*.—Smooth, glabrous.

*Texture, lower surface*.—Mostly smooth and glabrous with sparse pubescence along midvein; venation, prominent.

*Venation pattern*.—Pinnate.

*Color*.—Developing and fully expanded leaves, upper surface: Close to 146A tinged with close to 166A; edges, close to 166A; venation, close to N144D. Developing and fully expanded leaves, lower surface: Close to 147B tinged with close to 166A; edges, close to 166A; venation, close to N144D.

*Petioles*.—Length: About 5 mm. Diameter: About 5 mm. Texture, upper and lower surfaces: Slightly pubescent. Color, upper and lower surfaces: Close to N144D.

Flower description:

*Flower arrangement and habit*.—Salverform flowers arranged in terminal clusters each with about three to six flowers; about 150 flowers develop per lateral stem and numerous flowers developing during the flowering season; flowers face upright to outwardly.

*Fragrance*.—Faintly fragrant; sweet and floral.

*Natural flowering season*.—Plants of the new *Weigela* flower remontantly from May until November in Michigan; flowers not persistent.

*Flower buds*.—Length: About 2 cm. Diameter: About 5 mm. Shape: Spatulate. Color: Close to 59A.

*Flower diameter*.—About 2.5 cm.

*Flower depth*.—About 3 cm.

*Flower throat diameter*.—About 1 cm.

*Flower tube length*.—About 2 cm.

*Flower tube diameter, proximally*.—About 2 mm.

*Corolla*.—Arrangement: Salverform; five petals fused into a tube with separate petal lobes. Petal lobe length: About 1 cm. Petal lobe width: About 1 cm. Petal lobe shape: Rounded. Petal lobe apex: Obtuse. Petal lobe margin: Entire. Petal texture, upper and lower surfaces: Smooth, glabrous; silky. Throat texture: Smooth, glabrous. Tube texture: Glabrous, some creasing. Color: Developing petal lobes, upper and lower surfaces: Close to 59C. Fully expanded petal lobes, upper and lower surfaces: Close to 59C; venation, close to 59C. Throat: Close to 59C; venation, close to 59C. Tube: Close to 59C; venation, close to 59C.

*Sepals*.—Quantity per flower: Five in a single whorl, fused at the base; calyx campanulate. Length: About 1 cm. Width: About 2 mm. Shape: Narrowly triangular. Apex: Acute. Margin: Entire. Texture, upper surface: Smooth; glabrous. Texture, lower surface: Slightly pubescent. Color, upper and lower surfaces: Close to N199A.

*Peduncles*.—Length: About 1 cm. Diameter: About 2 mm. Strength: Strong. Aspect: About 45 degrees from lateral branch axis. Texture: Smooth, glabrous. Color: Close to N199B.

*Reproductive organs*.—Stamens: Quantity and arrangement: Five per flower. Filament length: About 1 cm. Filament color: Close to 58C. Anther shape: Linear. Anther length: About 4 mm. Anther color: Close to 158A. Pollen amount: Abundant. Pollen color: Close to 158A. Pistils: Quantity: One per flower. Pistil length: About 3 cm. Style length: About 3 cm. Style color: Close to 161C. Stigma shape: Globular, lobed. Stigma color: Close to 150D. Seeds and fruits: To date, seed and fruit development has not been observed on plants of the new *Weigela*.

Garden performance: Plants of the new *Weigela* have exhibited good garden performance and to tolerate wind, rain and temperatures ranging from −31 C to 38 C.

Pathogen & pest resistance: To date, plants of the new *Weigela* have not been observed to be resistant to pathogens and pests common to *Weigela* plants.

It is claimed:

1. A new and distinct *Weigela* plant named 'SMNW9RB' as illustrated and described.

* * * * *